(12) United States Patent
Jean et al.

(10) Patent No.: US 10,732,190 B2
(45) Date of Patent: Aug. 4, 2020

(54) METHOD AND SYSTEM FOR PREDICTING AN ENGINE CONDITION

(71) Applicant: PRATT & WHITNEY CANADA CORP., Longueuil (CA)

(72) Inventors: Maurice Jean, Boucherville (CA); Frederic Busnel, Montreal (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 234 days.

(21) Appl. No.: 15/884,561

(22) Filed: Jan. 31, 2018

(65) Prior Publication Data
US 2019/0234971 A1    Aug. 1, 2019

(51) Int. Cl.
| | |
|---|---|
| *G01N 35/00* | (2006.01) |
| *G01N 33/28* | (2006.01) |
| *F02D 41/22* | (2006.01) |
| *G01N 31/22* | (2006.01) |
| *G01M 15/14* | (2006.01) |
| *F02C 9/00* | (2006.01) |
| *G05B 23/02* | (2006.01) |
| *G01N 15/02* | (2006.01) |

(52) U.S. Cl.
CPC ......... *G01N 35/00623* (2013.01); *F02C 9/00* (2013.01); *F02D 41/22* (2013.01); *G01M 15/14* (2013.01); *G01N 31/22* (2013.01); *G01N 33/2888* (2013.01); *F05D 2260/80* (2013.01); *G01N 15/02* (2013.01); *G01N 2035/00653* (2013.01); *G05B 23/0283* (2013.01)

(58) Field of Classification Search
None
See application file for complete search history.

(56) References Cited

U.S. PATENT DOCUMENTS

| | | | |
|---|---|---|---|
| 3,981,584 A | 9/1976 | Guymer | |
| 5,210,704 A | 5/1993 | Husseiny | |
| 5,517,427 A | 5/1996 | Joyce | |
| 5,572,320 A | 11/1996 | Reintjes et al. | |
| 2002/0112529 A1* | 8/2002 | Bondarowicz | G01N 33/2888 73/53.05 |
| 2005/0114088 A1 | 5/2005 | Gorden et al. | |
| 2014/0121994 A1* | 5/2014 | Jean | G01N 33/2858 702/27 |
| 2016/0370341 A1 | 12/2016 | Jean et al. | |
| 2017/0307583 A1 | 10/2017 | Jean | |

\* cited by examiner

*Primary Examiner* — Matthew D Krcha
(74) *Attorney, Agent, or Firm* — Norton Rose Fulbright Canada LLP

(57) ABSTRACT

Systems and methods for predicting a condition of an engine are described herein. A fluid sample having particles suspended therein is received from the engine. A plurality of particles are extracted from the fluid sample. A sample profile of the plurality of particles extracted from the fluid sample is obtained. A reference profile of particles of a reference fluid sample from a reference engine is obtained. The reference profile and the sample profile having particles identified based on size, aspect ratio and chemical composition. A correlation index between the sample profile and the reference profile is determined based on size and aspect ratio of the particles of the sample profile and the reference profile. A prediction that the engine has a known condition associated with the reference engine is generated from the correlation index. An output indicating the condition of the engine is generating based on the prediction.

18 Claims, 11 Drawing Sheets

METHOD AND SYSTEM FOR PREDICTING AN ENGINE CONDITION

TECHNICAL FIELD

The present disclosure relates generally to comparing fluid samples, and, more particularly, to comparing a fluid sample with a reference sample to predict an engine condition.

BACKGROUND OF THE ART

The analysis of engine oil or other lubricant for the purpose of identifying premature component wear has been performed for several decades using optical atomic spectroscopy (e.g., atomic emission spectroscopy (AES), as well as atomic absorption spectroscopy (AAS)). This technology was the basis for the military aviation's Spectroscopic Oil Analysis Program (SOAP). However, optical atomic spectroscopy has certain disadvantages, such as a lack of repeatability among different equipment and an inability to analyze particles greater than 5 µm in diameter. Furthermore, optical atomic spectroscopy is an elemental analysis of the total oil sample and typically does not characterize individual particles in the sample.

While there are existing techniques for fluid analysis from engines, there is still a need for improved methods and system for predicting engine conditions.

SUMMARY

There is described herein methods and systems for predicting an engine condition. The methods and systems for predicting an engine condition described herein may be used to predict an engine condition of an aircraft engine or any other suitable engine. The methods and systems for predicting an engine condition described herein utilize a technique for sample comparison referred to as a zoning and profiling approach.

In one aspect, there is provided a method for predicting an engine condition of an engine. The method comprises receiving a fluid sample from the engine, the fluid sample having particles suspended therein. The method comprises extracting a plurality of particles from the fluid sample. The method comprises obtaining a sample profile of the plurality of particles extracted from the fluid sample and obtaining a reference profile of particles of a reference fluid sample from a reference engine, the reference profile and the sample profile having particles identified based on size, aspect ratio and chemical composition. The method comprises determining a correlation index between the sample profile and the reference profile based on size and aspect ratio of the particles of the sample profile and the reference profile. The method comprises generating, from the correlation index, a prediction that the engine has a known condition associated with the reference engine. The method comprises generating, based on the prediction, an output indicating the condition of the engine.

In another aspect, there is provided a system for predicting an engine condition of an engine. The system comprises one or more devices for receiving a fluid sample from the engine, the fluid sample having particles suspended therein and extracting a plurality of particles from the fluid sample. The system comprises a non-transitory computer-readable memory having stored thereon program instructions executable by the at least one processing unit for: obtaining a sample profile of the plurality of particles extracted from the fluid sample and obtaining a reference profile of particles of a reference fluid sample from a reference engine, the reference profile and the sample profile having particles identified based on size, aspect ratio and chemical composition; determining a correlation index between the sample profile and the reference profile based on size and aspect ratio of the particles of the sample profile and the reference profile; generating, from the correlation index, a prediction that the engine has a known condition associated with the reference engine; and generating, based on the prediction, an output indicating the condition of the engine.

In another aspect, there is provided a computer readable medium having stored thereon program code executable by a processor for predicting an engine condition, the program code comprising instructions for implementing the method for predicting an engine condition.

DESCRIPTION OF THE DRAWINGS

Reference is now made to the accompanying figures in which.

It will be noted that throughout the appended drawings, like features are identified by like reference numerals.

DETAILED DESCRIPTION

Figure 1:
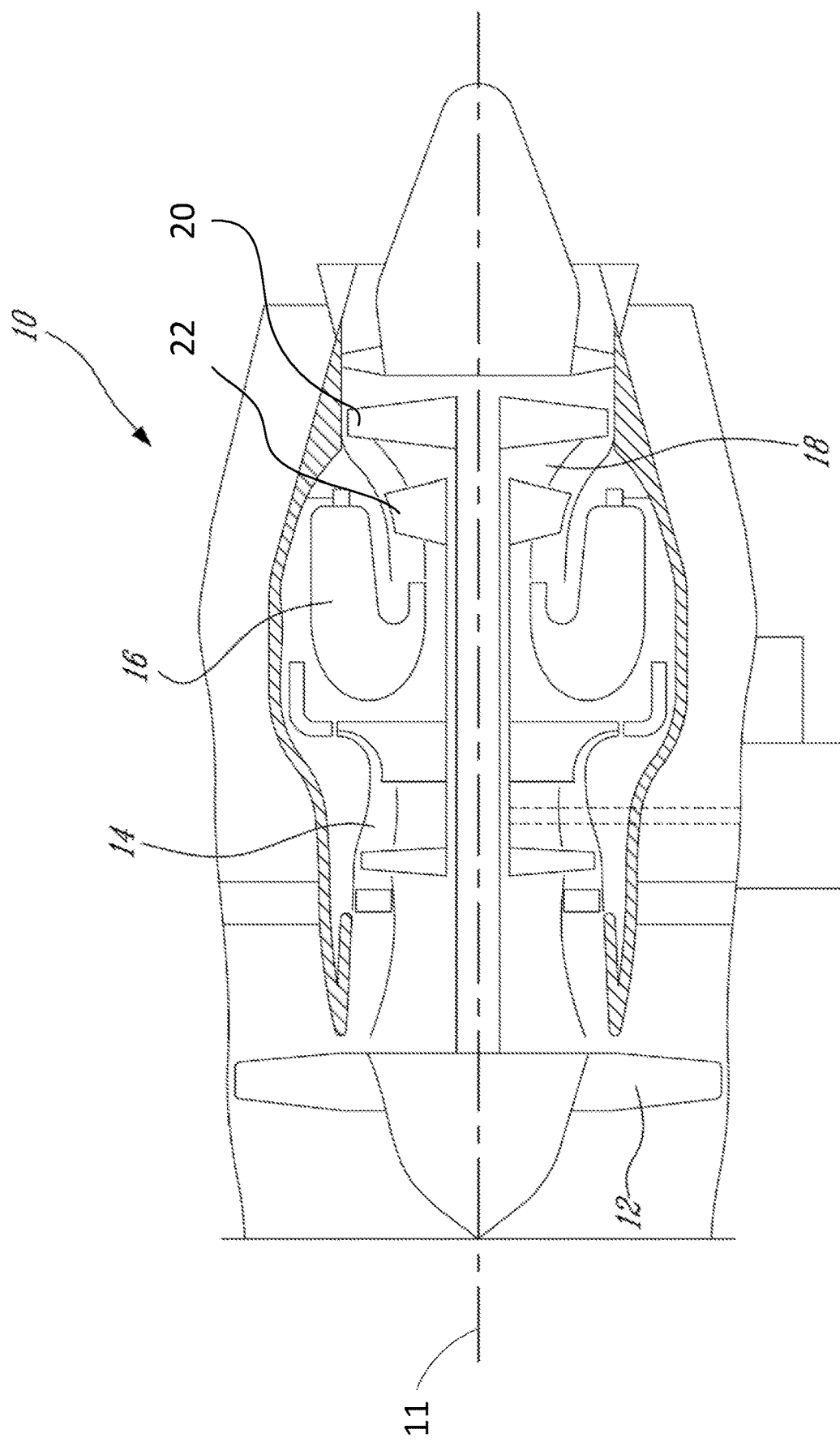
FIG. 1 is a schematic cross-sectional view of an example engine of an aircraft.

FIG. 1 illustrates a gas turbine engine 10 to which the methods and systems described herein may be applied. Note that while engine 10 is a turbofan engine, the methods and systems described herein may be applicable to turboprop, turboshaft, and other types of engines. Engine 10 generally comprises in serial flow communication: a fan 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases. Axis 11 defines an axial direction of the engine 10. In some embodiments, a low pressure spool is composed of a low pressure shaft and a low pressure turbine 20. The low pressure shaft drives the fan 12. A high pressure spool is composed of a high pressure turbine 22 attached to a high pressure shaft, which is connected to the compressor section 14.

Figure 2A:
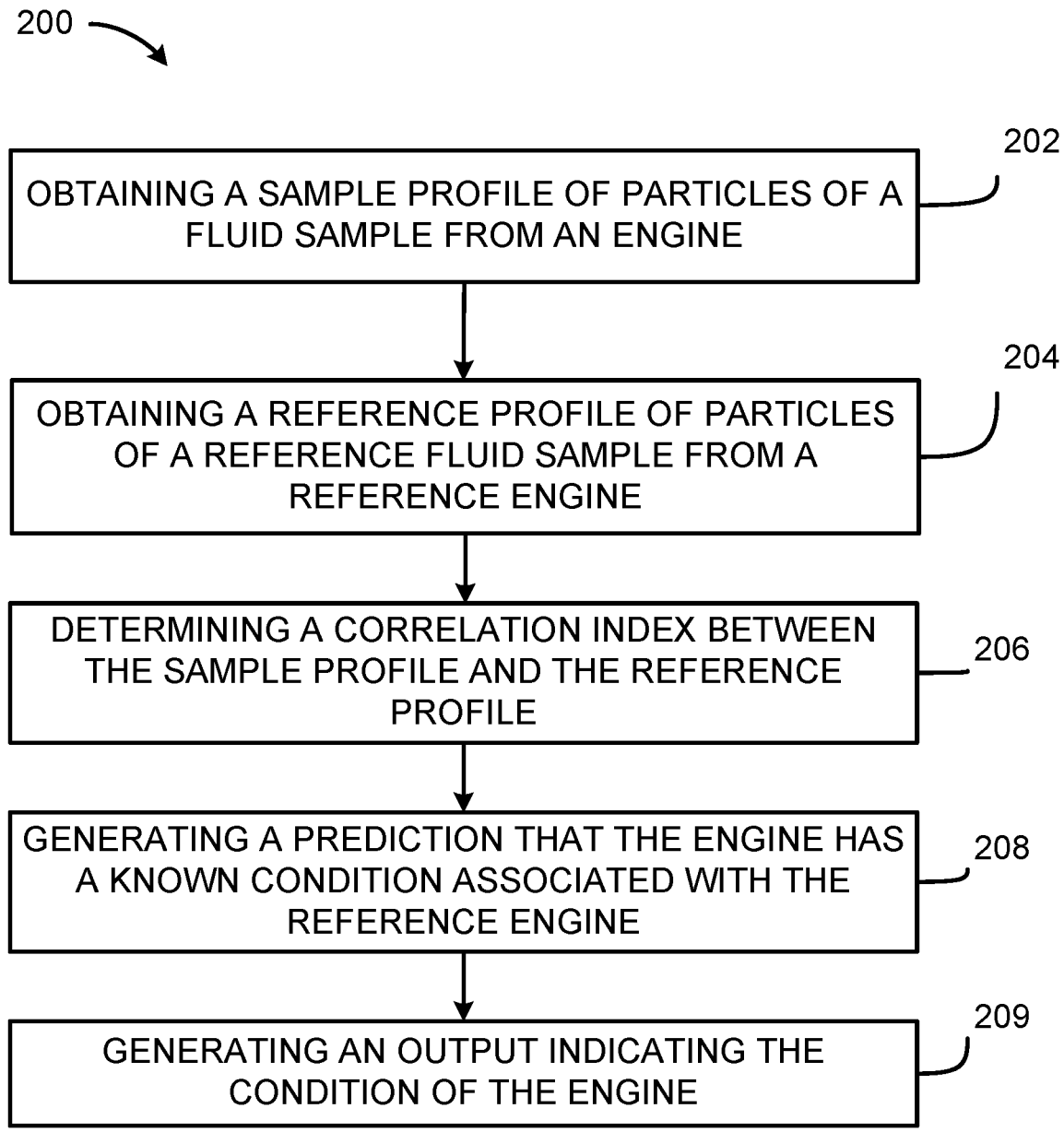
FIG. 2A is a flowchart illustrating an example method for predicting an engine condition in accordance with an embodiment.

With reference to FIG. 2A, there is shown a flowchart illustrating an example method 200 for determining a similarity between two fluid samples and for predicting a condition of an engine, such as the engine 10 of FIG. 1. While the method 200 is described herein with reference to the engine 10 of FIG. 1, this is for example purposes. The method 200 may be applied to other types of engines depending on practical implementations.

In some embodiments, parts of the method 200 may be performed using aspects described by co-owned United States patent applications bearing publication Nos. 2014/0121994 and 2016/0370341, the contents of which are hereby incorporated by reference.

At step 202, a profile of particles of a fluid sample from the engine 10 is obtained. The profile has particles identified from the fluid sample based on parameters including, but not limited to, one or more physical characteristics (e.g., size, aspect ratio and/or any other suitable physical characteristics) and chemical composition. In accordance with a specific and non-limiting example of implementation, the profile has particles identified from the fluid sample based on size, aspect ratio and chemical composition. Size refers to the longest dimension of a particle (i.e., maximum diameter). Aspect ratio refers to the longest dimension of a particle divided by the smallest dimension of the particle (i.e., a ratio of the longest dimension and the smallest dimension). The profile of particles is a data representation of particles. The engine 10 may be considered as an engine under test. The parameters may be referred to as features.

While some examples described herein are with reference to a profile of particles obtained from a single fluid sample, it should be understood that a plurality of profiles may be obtained from one or more fluid samples. For example, each one of the plurality of profiles may be obtained from a respective one of a plurality of fluid samples from the engine 10.

In accordance with an embodiment, the profile of particles is determined from a plurality of particles of a fluid sample based on a chemical composition of each particle satisfying a chemical composition criteria and based on physical characteristics (e.g., size and aspect ratio) of each particle satisfying a profile criteria. The process of determining a profile of particles based on each particle satisfying a chemical composition criteria and physical characterises (e.g., size and aspect ratio) of each particle satisfying a profile criteria is referred to herein as a zoning and profiling approach. The process of identifying particles satisfying the chemical composition criteria is referred to herein as zoning. In other words, zoning refers to using chemical composition criteria to select particles from which a profile is ultimately established. The term "zone" may be used to refer to the particles that satisfy the chemical composition criteria. The process of characterizing particles using size and aspect ratio is referred to herein as profiling.

In accordance with an embodiment, the profile of particles is determined by receiving the fluid sample having particles suspended therein from the engine 10, extracting a plurality of particles from the fluid sample, and obtaining the sample profile from the plurality of particles extracted from the fluid sample by identifying particles based on size, aspect ratio and chemical composition.

At step 204, a reference profile of particles of a reference fluid sample is obtained. The reference profile has particles identified from the reference sample based on parameters including, but not limited to, one or more physical characteristics (e.g., size, aspect ratio and/or any other suitable physical characteristics) and chemical composition. In accordance with a specific and non-limiting example of implementation, the reference profile has particles identified from the reference fluid sample based on size, aspect ratio and chemical composition. At step 204, the reference profile of particles may be obtained in a similar manner as the profile at step 202. The profile of particles at step 202 may be referred to as a "sample profile" to differentiate from the "reference profile" of particles obtained of step 204. The reference profile of particles is a data representation of particles.

While some examples described herein are with reference to a reference profile of particles obtained from a single reference fluid sample, it should be understood that a plurality of reference profiles may be obtained from one or more reference fluid samples. For example, each one of the plurality of reference profiles may be obtained from a respective one of a plurality of reference fluid samples.

The reference fluid sample may be from the same engine 10 or may be from a different engine. For example, the reference fluid sample may be from a reference engine of a similar type or build as the engine 10. In accordance with an embodiment, the reference engine is the engine 10. In accordance with an embodiment, an engine condition of the reference engine is known and may be referred to as a known engine condition.

The known engine condition may correspond to a negative performance indicator, such as a condition of one or more components of a given engine, a failure of a given engine, a failure of a given component of a given engine, a predicted mechanism of failure. The known engine condition may correspond to a positive performance indicator of the engine such as a normal condition of a given engine or a normal condition of one or more components of a given engine or a given engine. The known engine condition may correspond to any other suitable engine condition. Examples of predicted mechanism of failure include excess vibration, bearing wear, external contamination following engine maintenance, bearing rubbing, gear degradation, and bearing cage and race degradation, among others. In some embodiments, the chemical composition criteria may be determined based on a known failure mechanism. Accordingly, the reference engine may have the known engine condition such that the reference profile of particles may be used as a reference to predict if another engine (e.g., engine 10) is likely to have the same known engine condition as the reference engine.

In some embodiments, the reference profile of particles is predetermined prior to performance of method 200 and is stored in a database. In some embodiments, obtaining the reference profile of particles comprises obtaining the reference profile of particles from a database. In some embodiments, data representing a plurality of particles filtered from the reference fluid sample is obtained from the database and processing is performed to determine the reference profile of particles.

At step 206, a correlation index is determined between the sample profile and the reference profile. In accordance with an embodiment, the correlation index is determined between the sample profile and the reference profile for a specific zone. In accordance with an embodiment, the correlation index is determined based on physical characteristics of the particles of the sample profile and the reference profile. The determination of the correlation index may vary depending on practical implementations. For example, where a plurality of profiles is obtained, the correlation index may be determined differently from when a single sample profile is obtained. Similarly, when a plurality of zones are used, the correlation index may be determined differently from when a single zone is used.

In accordance with an embodiment, the correlation index is determined between the sample profile and the reference profile based on size and aspect ratio of the particles of the sample profile and the reference profile. In this example, the correlation index represents a correlation between a distribution of particles in both sample profile and reference profile as a function of size and aspect ratio of the particles of the sample profile and the reference profile.

It should be appreciated that depending on the value of the correlation index, the correlation index may represent a degree of similarity between two fluid samples.

At step 208, a prediction of a condition of the engine 10 is generated from the correlation index. In accordance with an embodiment, the prediction is that the engine 10 has the known condition of the reference engine associated with the reference fluid sample. The known condition of the reference engine may be considered applicable to the engine 10 based on the correlation index. For example, the know condition may be predicted to be applicable to the engine 10 when the correlation index is above a threshold The threshold may vary depending on practical implementation. For example the threshold may be 0.95 (or 95%), 0.9 (or 90%), 0.85 (or 85%), or any other suitable value. The threshold may be determined based on the known engine condition of the reference engine. Similarly, the threshold may be determined based on chemical composition criteria and/or the profile criteria. The threshold may indicate a level of similarity between the fluid sample from the engine 10 and the reference fluid sample. In some embodiments, predicting the condition of the engine comprises determining a level of similarity between the fluid sample from the engine 10 and the reference fluid sample based on the correlation index (e.g., by comparing of the correlation index to the threshold) and establishing the condition of the engine based on the known condition of the reference engine from which the reference fluid sample was obtained.

Predicting the engine condition may comprise determining if there is a low, moderate or high chance of the engine 10 having the engine condition. For example, if the correlation index is between 0 and 50% then this may indicate a low chance of the engine 10 having the engine condition; if the correlation index is between 50 and 80% then this may indicate a moderate chance of the engine 10 having the engine condition; and if the correlation index is between 80 and 100% then this may indicate a high change of the engine having the engine condition. The ranges for predicting if the engine 10 has a low, moderate or high chance of having the engine condition may vary depending on practical implementation. Similarly, the classifications of low, moderate or high may vary to have more or less than three classes.

In some embodiments, predicting the engine condition may comprise determining a likelihood that the engine 10 has the known condition of the reference engine. For example, the correlation index may be indicative of the likelihood that the engine 10 has the known condition of the reference engine.

In accordance with an embodiment, at step 209, an output is generated indicating the condition of the engine 10 based on the prediction at step 208. In accordance with an embodiment, the output indicates the prediction of the engine condition as generated at step 208. The output may indicate that the engine 10 has a likelihood of having the known condition of the reference engine. The output may indicate the negative performance indicator or the positive performance indicator. The output may indicate when the engine is expected to fail, the mechanism of failure of the engine and/or any other suitable information.

Figure 2B:
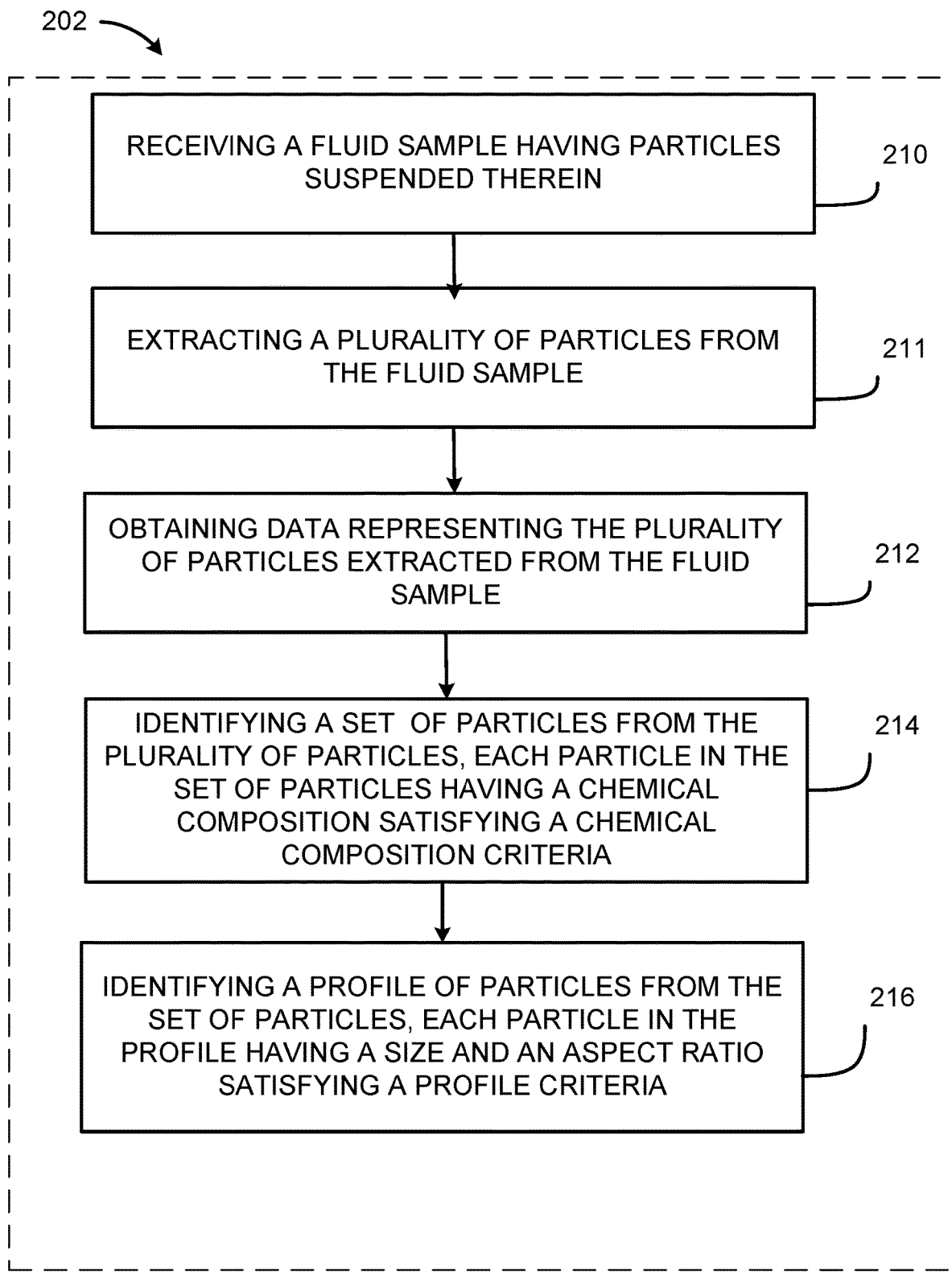
FIG. 2B is a flowchart illustrating an example method for obtaining a profile of particles by zoning and profiling in accordance with an embodiment.

With additional reference to FIG. 2B, a flowchart illustrates an example of obtaining a profile of particles of a fluid sample in accordance with an embodiment of step 202. In other words, FIG. 2B illustrates an example embodiment of zoning and profiling. At step 210, the fluid sample having particles suspended therein is received from the engine 10. The fluid sample may be an oil or other lubricant sample removed from the engine 10. In the example of an oil sample from an aircraft engine, the oil sample may be collected by the aircraft operator. In some examples, more than one sample may be obtained from the engine 10. A relatively small amount of oil (e.g., 25 mL or less) may be sufficient. The amount of oil sample obtained may be selected in order to obtain a certain number of particles suspended therein. For example, it may be known or expected that a given engine should have a certain concentration of particles in the oil after a certain number of operating hours. The volume of oil sample obtained may thus be determined in order to obtain a minimum quantity of particles. The sample may be obtained and prepared using any suitable method.

At step 211, a plurality of particles are extracted from the fluid sample removed from the engine 10. The particles are extracted from the fluid sample using any suitable method. In accordance with an embodiment, particles extracted are relatively small particles that are not typically captured by conventional engine oil filters. Indeed, an engine oil filter typically only filters large particles and/or an oil plug of an engine typically only has large particles stuck thereon. It should be appreciated that, by using relatively small particles for analysis according to methods and/or systems described herein, a more accurate prediction of an engine condition may ultimately be obtained as large particles may not provide an accurate time indicator of a condition of the engine. Furthermore, removing debris from an engine oil filter is usually costly as the engine oil filter typically cannot be reused. Moreover, removing an engine oil filter may be time consuming.

In some embodiments, a collected oil sample may be filtered using a very fine filter, such as a 0.22 $\mu$m filter, in order to filter out particles of a given size (e.g., particles having a diameter of 0.22 $\mu$m or more). The particles obtained may range in size from about 0.22 $\mu$m to about 1600 $\mu$m, for example, although particles of other sizes may also be obtained. The volume of oil sample filtered and the size of the sample prepared may vary, such as according to the number of particles in the oil. The volume of oil sample that is filtered may be determined based on the type of engine and/or the expected normal levels of particles in the oil.

In some embodiments, the extracted particles are cleaned to remove any residue (e.g., oil). For example, a solvent may be used to clean the particles. Any other suitable technique for cleaning the particles may be used.

At step 212, data representing a plurality of particles extracted from the fluid sample is obtained. In accordance with an embodiment, raw data representing a plurality of features of each of the plurality of particles extracted from the fluid sample is collected at step 212. Each particle is analyzed to determine a plurality of features, such as one or more physical characteristics (e.g., aspect ratio and size) and/or chemical composition (e.g., alloy type and chemical composition). In accordance with an embodiment, an x-ray spectroscopy device comprising one or more emitters and one or more detectors is used for this analysis. A scanning electron microscope (SEM) equipped to perform x-ray spectroscopy may be used for this analysis, although any other suitable methods may also be used. In accordance with an embodiment, the SEM produces images of the particles by scanning the particles with a focused beam of electrons. In accordance with an embodiment, the SEM comprises one or more emitters for emitting the beam of electrons. The emitted electrons interact with atoms of the particles, producing signals that contain information about the particles' surface topography and/or composition. In accordance with an embodiment, SEM comprises one or more detectors for collecting electronics (e.g., secondary electrons emitted by atoms excited by the electron beam). The signals collected by the collected electrons may be processed to produce signals that contain information about the sample's surface topography and/or composition. In accordance with an embodiment, an X-Ray Fluorescence (XRF) device is used for carrying out particles analysis. XRF is a non-destructive analytical technique used to determine the elemental composition of materials. In accordance with an embodiment, the XRF device comprises one or more emitters for emitting x-rays and one or more detectors for measuring the fluorescent (or secondary) x-ray emitted from the particles when they are excited by the one or more emitters. The XRF device may process the measured fluorescent x-ray and determine the chemical composition of the particles. In some embodiments, the SEM may be coupled to an X-Ray Fluorescence (XRF) detector and/or device for carrying out particle analysis. For example, an automated SEM may be used. Software and/or hardware in the system may automatically recognize the presence of a particle and may then automatically move a stage and an electron beam on the particle to perform the particle analysis. The particle chemical composition, size and/or aspect ratio may also be determined automatically. Any other suitable equipment may be used to perform this analysis.

Suitable image analyzer software, such as those conventionally used with SEM, may be used to collect data about particle physical characteristics and/or chemical composition. Analysis of each particle may produce a respective set of data for that particle, for example there may be up to 70 data points for each particle, the data describing various features of the particle (e.g., size, aspect ratio and chemical composition, among others).

The data obtained from this analysis may be further processed, in order to account for any measurement error and/or the possible presence of contamination. This further processing may be carried out by categorizing the particles as described below, where each particle is categorized based on the determined features (e.g., physical characteristics and/or chemical composition).

It should be appreciated that the conventional SOAP technique typically relies on elemental analysis using emission/atomic absorption analysis of particles. The particles analyzed are typically limited to 2-3 µm or smaller. The result of SOAP is typically a quantification of elements (e.g., iron) by volume (e.g., in ppm), without a consideration of the physical characteristics and the chemical composition of the particle, and may produce a relatively small number of data points (e.g., about 30 data points that describe the total quantities of individual elements in the total sample). In accordance with an embodiment of the present disclosure, the zoning and profiling approach considers physical characteristics and chemical composition of each individual particle, rather than overall characteristics of the total sample.

At step 214, a set of particles is identified from the plurality of particles, where each particle in the set of particles has a chemical composition satisfying a chemical composition criteria. Each particle may be categorized based on chemical composition and the plurality of particles may be identified from the categorization of each particle according to the chemical composition criteria. Categorization of particles may be based on, for example, the absolute chemical composition. Categories may be defined according to different alloy compositions, association with one specific manufacturing process and/or association with one particular source (e.g., engine component), for example. Categories may also be defined by the elemental composition or single material of the particles. By way of example, each particle may be categorized according to a percentage of each element (e.g., a particle may be categorized as 17.5% chromium, 7.5% nickel and 75% iron). The chemical composition criteria, for example, may be particles within respective ranges (i.e., lower and upper limits) of a percentage of each element (e.g., 10 to 20% chromium, 5 to 10% nickel, and 70 to 85% iron). In other words, in some embodiments, a chemical composition of a given particle satisfies the chemical composition criteria when a concentration range of at least one element of the given particle is within lower and upper limits that vary as a function of a given element. The chemical composition criteria when defined as one or more concentration ranges of a given particle may be referred to as a specific zone. In some embodiments, the chemical composition criteria is designed to ensure that the range of an element is large enough to contain a certain quantity of particles and small enough to limit to one type of material.

By way of another example, particles may be classified in a category such as "Environmental", "Metallic", "Non-metallic", "Plating", or "Miscellaneous", among others. Each particle may be further categorized into sub-category levels. As an example, the "Metallic" category may have a level 1 sub-category of "Copper", within which may be level 2 sub-categories of "Bronze" and "Brass". In some examples, five levels of decision may be used to categorize each particle into a specific level (e.g., metallic, copper, bronze, leaded bronze or machining chip). The chemical composition criteria may be one or more categories (e.g., the "Metallic" category with a sub-category of "Copper").

Categories may be defined according to a level of interaction and/or an interaction zone as described by co-owned United States patent application bearing publication No. 2016/0370341. For example, particles may be identified that fall within the interaction zone. The interaction zone may correspond to a concentration range for at least a first element found in a first material and at least a second element found in at least a second material, the concentration range may be defined by upper and lower limits that vary as a function of a given element, the upper limit may correspond to a minimum concentration for the given element in one of the first material and the second material, and the lower limit may correspond to a maximum concentration for the given element in the other of the first material and the second material. It should be appreciated that two parts made of different materials may generate debris that will be a mix of both materials and by measuring the mixture may help in identifying a failure involving these two parts.

At step 216, the profile of particles is identified from the set of particles, where each particle in the profile of particles has a size and aspect ratio satisfying a profile criteria. For example, the size and the aspect ratio of a given particle may satisfy the profile criteria when the size of the given particle is within lower and upper size limits and the aspect ratio of the given particle is within lower and upper aspect ratio limits. The lower and upper size limits and the lower and upper aspect ratio limits may be set according to percentiles of the size and aspect ratio of the particles in the set of particles. In other words, the lower size limit may be a lower percentile limit of the size of the particles in the set of particles, the upper size limit may be an upper percentile limit of the size of the particles in the set of particles, the lower aspect ratio limit may be a lower percentile limit of the aspect ratio of the particles in the set of particles and the upper aspect ratio limit may be an upper percentile limit of the aspect ratio of the particles in the set of particles. For example, the profile of particles may be identified from the set of particles based on each particle in the profile of particles having a size within a 20 to 80 percentile of the sizes of the particles of the set of particles and having an aspect ratio within a 20 to 80 percentile of the aspect ratios of the particles of the set of particles. By way of another example, the lower and upper size limits and the lower and upper aspect ratio limits may be numerical value limits (e.g., a size between 0.8 μm and 2.8 μm and an aspect ratio between 1.2 and 2.4). The lower and upper size limits and the lower and upper aspect ratio limits may vary depending on practical implementations.

Similarly, the steps 212, 214 and 216 of FIG. 2B may be used to determine the reference profile of particles. In accordance with an embodiment, the chemical composition criteria and/or the profile criteria at step 204 is the same as described at step 202.

Figure 3A:
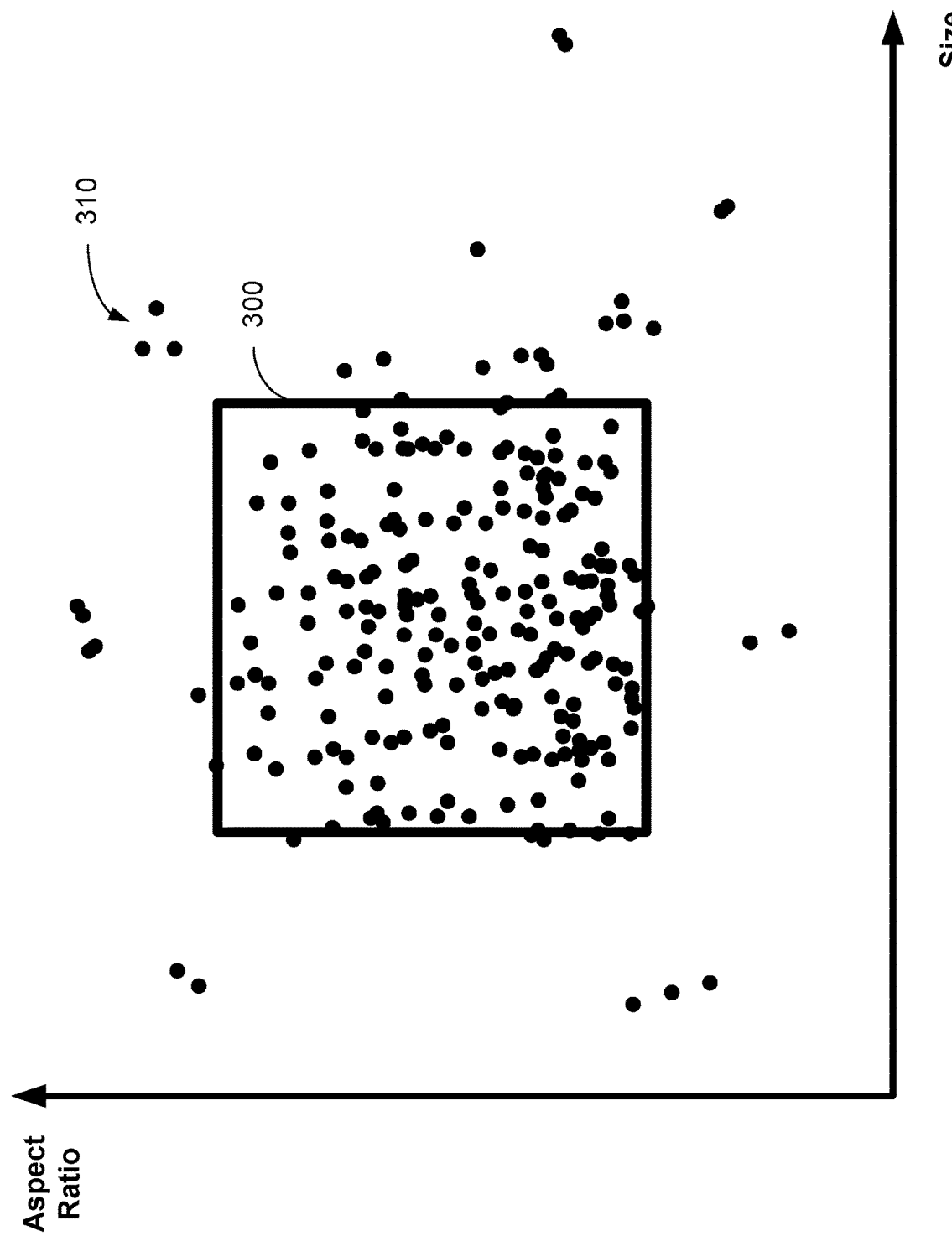
FIG. 3A is a graphical representation of a first profile of particles in accordance with an embodiment.

With reference to FIG. 3A, an example of a sample profile 300 of particles and a first set 310 of particles is shown. In this example, each particle in a first set 310 satisfies the chemical composition criteria. The particles in the sample profile 300 is a subset of particles from the first set 310, where each particle in the sample profile 300 satisfies the profile criteria. With additional reference to FIG. 3B, an example of a reference profile 400 of particles and a second set 410 of particles is shown in combination with the sample profile 300 and the first set 310. For the purposes of illustrative clarity, the particles in the first set 310 are represented by solid circles and the particles in the second set 410 are represented by unfilled circles. In this example, each particle in the second set 410 satisfies the chemical composition criteria. The particles in the reference profile 400 are a subset of particles from the second set 310, where each particle in the reference profile 400 satisfies the profile criteria. As illustrated, the sample profile 300 has a center 320 and the reference profile 410 has a center 420. In accordance with an embodiment, the center of a profile is defined as the $50^{th}$ percentile for size and the $50^{th}$ percentile for aspect ratio of the particles in a given profile. In this example, the center 320 is the $50^{th}$ percentile for size and the $50^{th}$ percentile for aspect ratio of the particles in the sample profile 300. Similarly, in this example, the center 420 is the $50^{th}$ percentile for size and the $50^{th}$ percentile for aspect ratio of the particles in the reference profile 400. As described in further detail elsewhere in this document, the sample profile 300 and the reference profile 400 are used to compare the fluid sample from the engine 10 and the reference fluid sample to determine a similarity between the fluid samples.

Figure 2C:
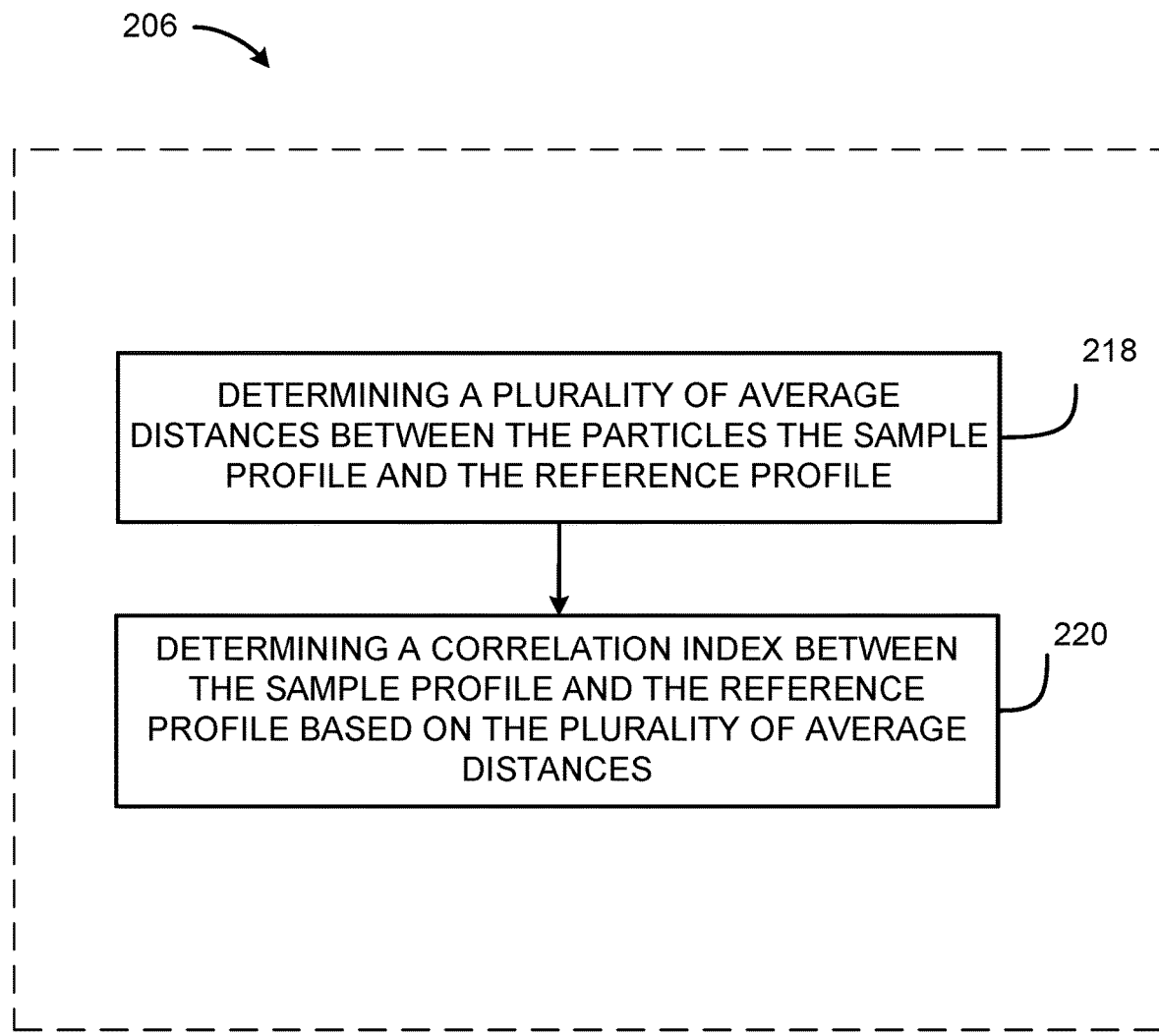
FIG. 2C is a flowchart illustrating an example method for determining a correlation index between particles in the sample and reference profiles in accordance with an embodiment.
Figure 3B:
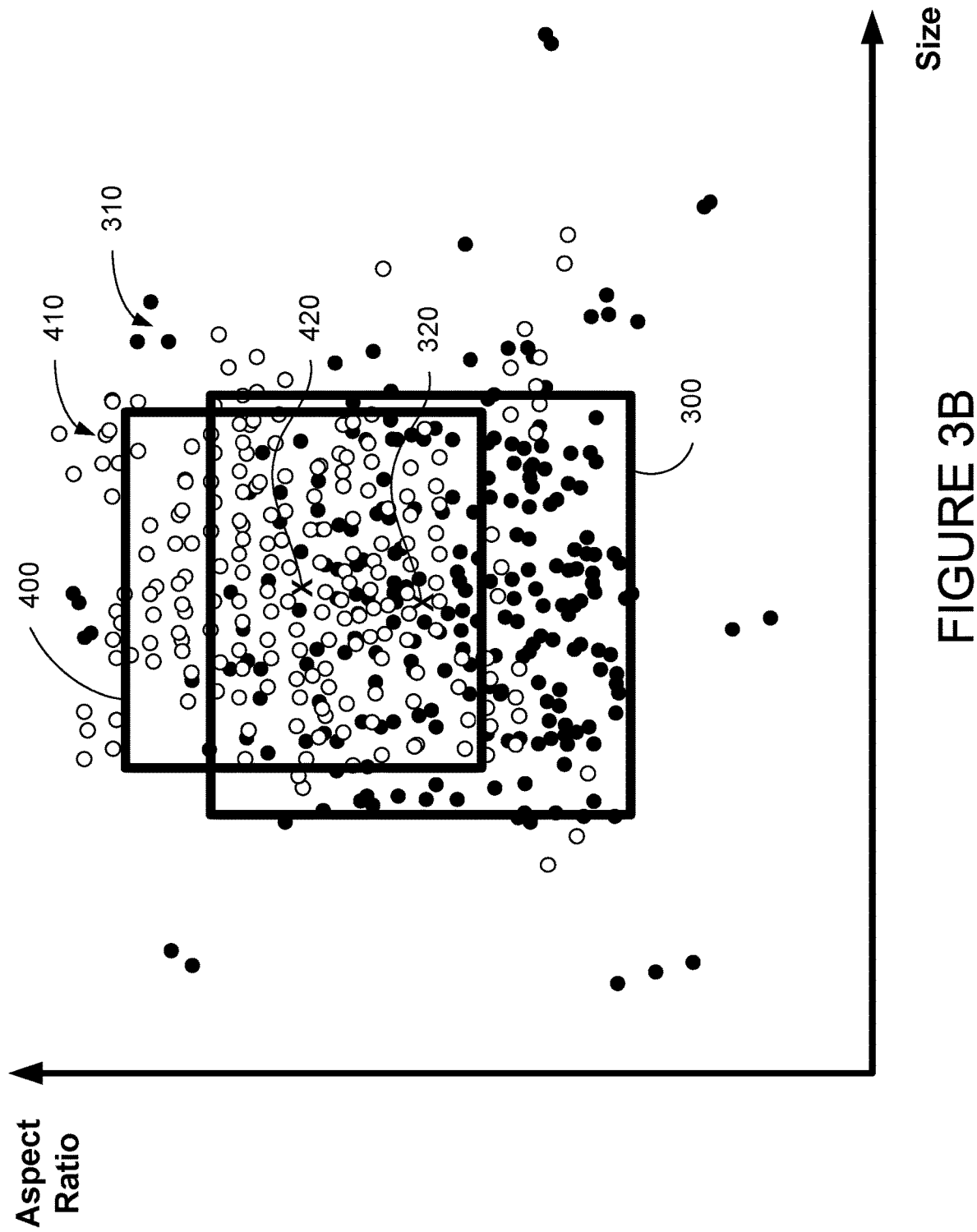
FIG. 3B is a graphical representation of the first profile of particles and a second profile of particles in accordance with an embodiment.

With additional reference to FIG. 2C, a flowchart illustrates an example of determining the correlation index between the particles in the sample profile 300 and the reference profile 400 in accordance with an embodiment of step 206. At step 218, a plurality of average distances is determined between particles in each of the sample profile 300 and the reference profile 400 and a respective center 320, 420 of each of the sample profile 300 and the reference profile 400. In accordance with an embodiment, the plurality of average distances is determined using size and aspect ratio as axes of a two-dimensional coordinate system used to position particles in a two-dimensional Euclidean space. For example, a first axis of the coordinate system may correspond to size and a second axis of the coordinate system may correspond to aspect ratio (e.g., as shown in FIGS. 3A and 3B). At step 220, the correlation index is determined based on the plurality of average distances.

Figure 2D:
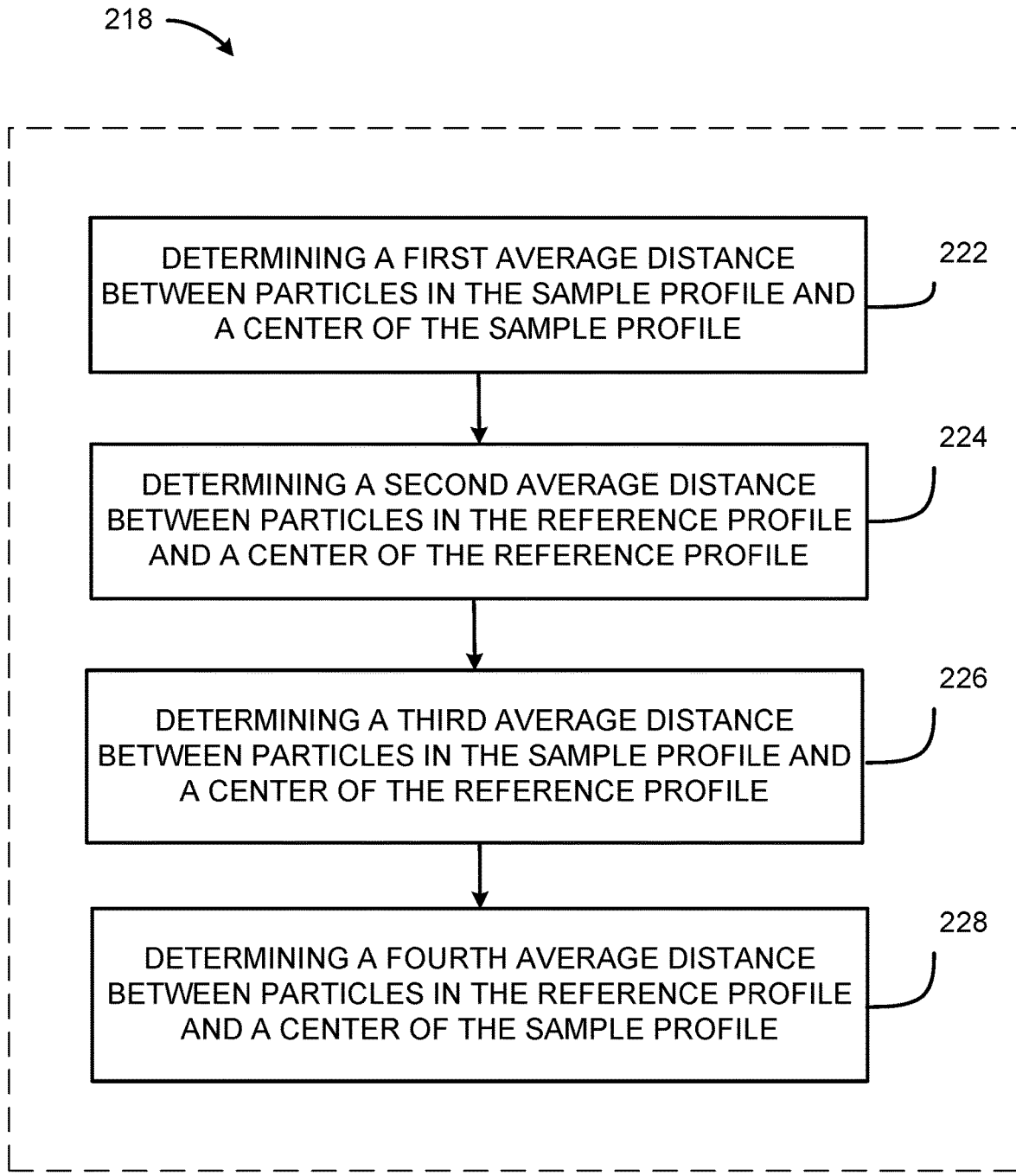
FIG. 2D is a flowchart illustrating an example method for determining a plurality of average distances between particles in each of a sample and a reference profile in relation to a center of each of the sample and reference profile in accordance with an embodiment.

With additional reference to FIG. 2D, a flowchart illustrates an example of determining the plurality of average distances between the sample profile 300 and the reference profile 400 in accordance with an embodiment of step 218 of FIG. 2C. At step 222, a first average distance between particles in the sample profile 300 and the center 320 of the sample profile 300 is determined.

The average distance may be referred to as an average mathematical distance (AMD). The AMD for a profile k is the square of the average distances between particles in the profile k and the mathematical center of profile k. The AMD for the profile k may be represented by equation (1):

$$AMD_{k.k} = \frac{\sum_{i}^{Nb_k}\left(\sqrt{Size_{k_i}} - \sqrt{Size_{MC_k}}\right)^2 + \left(\sqrt{Ratio_{k_i}} - \sqrt{Ratio_{MC_k}}\right)^2}{Nb_k}, \quad (1).$$

The subscript k.k indicates that the AMD has been calculated for particles in the profile k using the mathematical center of profile k. $Nb_k$ refers to the number of particles in the profile k. $Size_{k_i}$ refers to the size of the i-th particle in profile k and $Ratio_{k_i}$ refers to the aspect ratio of the i-th particle in profile k. $Size_{MC_k}$ refers to the $50^{th}$ percentile for size and $Ratio_{MC_k}$ refers to the $50^{th}$ percentile for aspect ratio for the particles in the profile k.

In accordance with an embodiment, the first average distance between particles in the sample profile 300 and the center 320 of the first profile 300 is determined according to equation (1). The first average distance may be represented by $AMD_{1.1}$.

At step 224, a second average distance between particles in the reference profile 400 and the center 420 of the reference profile 400 is determined. The center of the reference profile 400 may be defined as the $50^{th}$ percentile for size and the $50^{th}$ percentile for aspect ratio of particles in the reference profile. Similar to step 222, the second average distance between particles in the reference profile 400 and the center 420 of the reference profile 400 may be determined according to equation (1). The second average distance may be represented by $AMD_{2,2}$.

At step 226, a third average distance between particles in the sample profile 300 and the center 420 of the reference profile 400 is determined. The AMD for the profile k with the mathematical center of profile j is the square of the average distances between particles in the profile k and the mathematical center of profile j and may be represented by equation (2):

$$AMD_{k\cdot j} = \frac{\sum_{i}^{Nb_k}\left(\sqrt{Size_{k_i}} - \sqrt{Size_{MC_j}}\right)^2 + \left(\sqrt{Ratio_{k_i}} - \sqrt{Ratio_{MC_j}}\right)^2}{Nb_k}, \quad (2)$$

The subscript k.j indicates that the AMD has been calculated for particles in the profile k using the mathematical center of profile j. $Nb_k$ refers to the number of particles in the profile k. $Size_{k_i}$ refers to the size of the i-th particle in profile k and $Ratio_{k_i}$ refers to the aspect ratio of the i-th particle in profile k. $Size_{MC_j}$ refers to the $50^{th}$ percentile for size for profile j and $Ratio_{MC_j}$ refers to the $50^{th}$ percentile for aspect ratio for profile j.

In accordance with an embodiment, the third average distance between particles in the sample profile 300 and the center 420 of the reference profile 400 is determined according to equation (2). The third average distance may be represented by $AMD_{1,2}$.

At step 228, a fourth average distance between particles in the reference profile 400 and the center 320 of the sample profile 300 is determined. In a similar manner to that of step 224, the fourth average distance between particles in the reference profile 400 and the center 320 of the sample profile 300 may be determined according to equation (2). The fourth average distance may be represented by $AMD_{2,1}$.

Figure 2E:
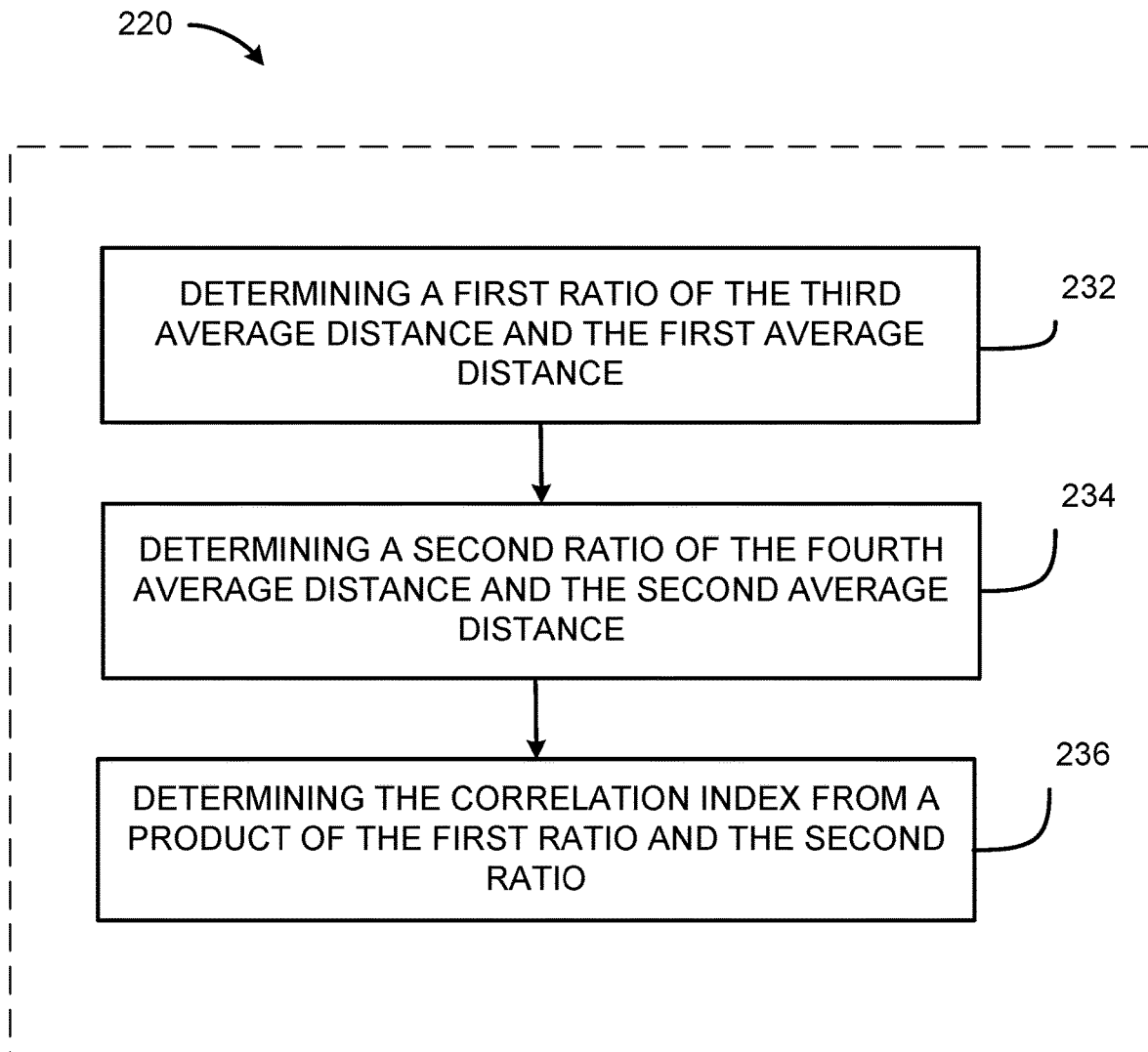
FIG. 2E is a flowchart illustrating an example method for determining a correlation index between particles in the sample and reference profiles from the plurality of average distances determined according to FIG. 2D in accordance with an embodiment.

With additional reference to FIG. 2E, a flowchart illustrates an example of determining the correlation index from the first, second, third and fourth average distances in accordance with an embodiment of step 220 of FIG. 2C. At step 232, a first ratio of the third average distance and the first average distance is determined. The ratio may be represented by equation (3):

$$\frac{AMD_{k\cdot j}}{AMD_{k\cdot k}}, \quad (3)$$

Equation (3) signifies a difference in the distribution of profile k using the mathematical center of profile j. In accordance with an embodiment, this reference is smaller than one; if the $AMD_{k,j}$ is greater than $AMD_{j,k}$, then the reverse ratio may be used.

The first ratio may be represented as:

$$\frac{AMD_{1,2}}{AMD_{1,1}}$$

At step 234, a second ratio of the fourth average distance and the second average distance is determined. Similar to step 232, the second ratio may be determined according to equation (3). The second ratio may be represented as:

$$\frac{AMD_{2,1}}{AMD_{2,2}}$$

At step 236, the correlation index is computed as a product of the first and second ratios. The correlation index may be determined by equation (4):

$$CI_{j\cdot k} = \frac{AMD_{k\cdot j}}{AMD_{k\cdot k}} \times \frac{AMD_{j\cdot k}}{AMD_{j\cdot j}}, \quad (4)$$

The correlation index for the sample profile 300 and the reference profile 400 may be represented by:

$$CI_{1,2} = \frac{AMD_{1,2}}{AMD_{1,1}} \times \frac{AMD_{2,1}}{AMD_{2,2}}$$

If the correlation index is equal to 1 (or 100%) this is indicative of perfect correlation between the sample profile 300 and the reference profile 400. The higher the correlation index, the higher a similarity between the sample profile 300 and the reference profile 400. Thus, for example, the correlation index may be indicative of a similarity between the engine 10 and the reference engine, when the chemical composition criteria and/or the profile criteria are designed to be indicative of an engine condition of the reference engine.

It should be appreciated that, in this example, the correlation index is used to determine the similarity between the sample profile 300 and the reference profile 400.

In some embodiments, the sample profile 300 may be represented by a first matrix and the reference profile 400 may be represented by a second matrix. One of the rows or columns of a given matrix may correspond to size and one of the rows or columns of the given matrix may correspond to aspect ratio. The matrix may be used to determine the correlation index.

In some embodiments, method 200 may be performed on a plurality of samples from the engine 10. For example, at step 202, obtaining the sample profile of particles may comprise obtaining a plurality of sample profiles of particles, where each one of the plurality of sample profiles of particles corresponds to a respective one of a plurality of fluid samples from the engine 10. Step 206 may be performed for each one of the plurality of samples in relation to the same reference profile of particles obtained at step 204. In this example, at step 218 of FIG. 2C, determining the plurality of average distances comprises determining average distances for each one of the plurality of sample profiles in relation to the same reference profile. In this example, step 220 of FIG. 2C comprises determining a plurality of profile correlation indices, where each profile correlation index is associated with a respective sample of the plurality of samples from the engine 10. A global correlation index may then be determined from the plurality of profile correlation indices. At step 208, the global correlation index may be used to predict the engine condition.

Figure 2F:
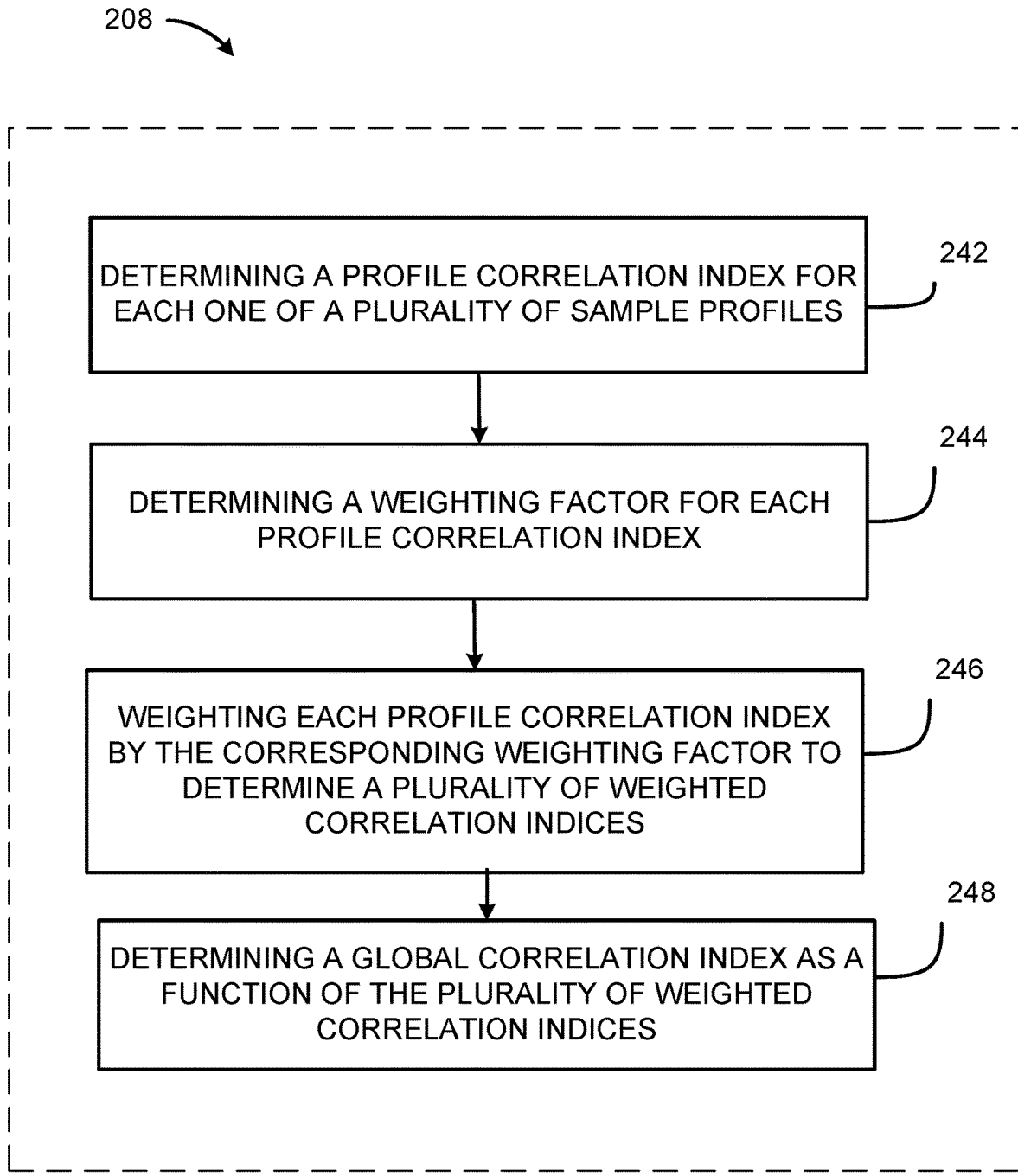
FIG. 2F is a flowchart illustrating an example method for determining a correlation index for a plurality of samples in accordance with an embodiment.

With reference to FIG. 2F, a flowchart illustrates an example of determining the correlation index when a plurality of samples are obtained from the engine 10 in accordance with an embodiment of step 208 of FIG. 2A. In this example, the resulting correlation index is referred to as the global correlation index. At step 242, a profile correlation index is determined for each one of the plurality of sample profiles. In accordance with an embodiment, each profile correlation index is determined based on average distances associated with a respective one of the plurality of sample profiles in relation to the reference profile of particles. For example, steps 222, 224, 226 and 228 of FIG. 2D may be performed for each one of the plurality of sample profiles in relation to the same reference profile to determine a plurality of average distances for each one of the plurality of sample profiles in relation to the reference profile. Similarly, steps 232, 234 and 236 of FIG. 2E may be performed for each one of the plurality of sample profiles and the result would be a plurality of profile correlation indices, each one associated with a respective profile of the plurality of sample profiles.

At step 244, a weighting factor for each profile correlation index is determined. In some embodiments, the weighting factor is determined based on a population of particles of a respective one of the plurality of sample profiles, because the number of particles (i.e., the population) in a given sample profile may vary. The weighting factor may be referred to as a population factor. The population factor for profile k and profile j may be referred to as $PF_{jk}$ and be represented by equation (5):

$$PF_{jk} = \frac{\log(Nb_j + 1)}{\log(Nb_k + 1)}, \qquad (5)$$

$Nb_k$ refers to the number of particles in the profile k and $Nb_j$ refers to the number of particles in the profile j. The population factor may be determined for each one of the plurality of sample profiles in respect to the same reference profile. In accordance with an embodiment, the population factor (PF) is a number equal to or less than 1; if $Nb_j$ is greater than $Nb_k$, the reverse of the ratio in equation (5) is used.

At step 246, a plurality of weighted correlation indices is determined based on weighting each profile correlation index by the corresponding weighting factor for each profile correlation index. For example, each profile correlation index may be multiplied by the corresponding population factor to determine the plurality of weighted correlation indices. If there are no particles in a given profile, the corresponding weighting factor for that profile may be set to 1 (or 100%).

At step 248, the global correlation index is determined as a function of the plurality of weighted correlation indices. For example, the global correlation index may be determined from a product of the plurality of weighted correlation indices. By way of another example, the global correlation index may be determined from the summation of the plurality of weighted correlation indices. The function for determining the global correlation index may vary depending on practical implementation and may comprise one or more of a product, summation, subtraction, division, and/or any other suitable arithmetic function or combination of functions. The global correlation index may then be used in step 208 of FIG. 2A as the correlation index used to predict the engine condition.

Referring back to FIG. 2A, in some embodiments, method 200 may be performed using a plurality of zones. In other words, a plurality of chemical composition criteria may be used to determine a plurality of sample profiles and reference profiles. For example, at step 202, obtaining the sample profile may comprise obtaining a plurality of sample profiles of particles, where each one of the plurality of sample profiles has particles with a chemical composition satisfying a respective one of a plurality of chemical composition criteria. Similarly, for example, at step 204, obtaining the reference profile may comprise obtaining a plurality of reference profiles of particles, where each one of the plurality of reference profiles has particles with a chemical composition satisfying a respective one of the plurality of chemical composition criteria. Step 206 may be performed for each one of the plurality of samples in relation to a respective one of the plurality of reference profiles of particles. In this example, at step 218 of FIG. 2C, determining the plurality of average distances comprises determining average distances for each one of the plurality of sample profiles in relation to a respective one of the reference profiles. In this example embodiment, step 220 of FIG. 2C comprises determining a plurality of zone correlation indices, where each zone correlation index is associated with a respective zone of the plurality of zones. A global correlation index may then be determined from the plurality of zone correlation indices. The global correlation index may be determined in a similar manner to that of steps 242, 244, 246 and 248 of FIG. 2F. At step 208, the global correlation index may be used to predict the engine condition. It should be appreciated that, in this example, the prediction at step 208 is based on a combination of two or more zones.

The determination of the plurality of zones may vary. For example, one or more zones may be selected with a high amount of particles. By way of another example, one or more zones may be selected where the zones correspond with a failure mode. The selection of the zones may be validated by comparing similar and non-similar samples. Accordingly, the threshold value for determining that the global correlation index is indicative of two fluid samples being similar may be established for every type of zone and/or sample.

In some embodiments, at step 208, a comparison with several reference samples with specific conditions may be used to predict a failure mechanism. For example, a high correlation index between the sample profile and the reference profile may be considered to be predictive of failure of a specific engine part, when the engine associated with the reference profile is known to have a failure of the engine part. The generated prediction may be recorded and saved for further action and/or future reference. Using the generated prediction, appropriate action may be taken. In some embodiments, corrective action(s) (e.g., engine removal or increased frequency of testing) may be determined based on the prediction. In some examples, prediction of expected failure and/or failure mechanism may involve review by an expert, a technical specialist and/or an operator. Where failure of a particular part has been predicted, the part may be replaced and/or monitored with greater frequency. Alternatively, where failure of the engine has been predicted, the engine may be placed on a tighter maintenance and/or oil analysis schedule. For example, the disclosed methods may include performing a maintenance or pre-maintenance action on the engine. Maintenance or pre-maintenance actions that may be performed include, for example, flagging the engine for maintenance (e.g., in a maintenance file), generating a notification to alert a user for the need to perform maintenance, scheduling maintenance for the engine, and performing the appropriate maintenance, among others. The maintenance or pre-maintenance action performed may be dependent on the generated prediction.

Figure 4:
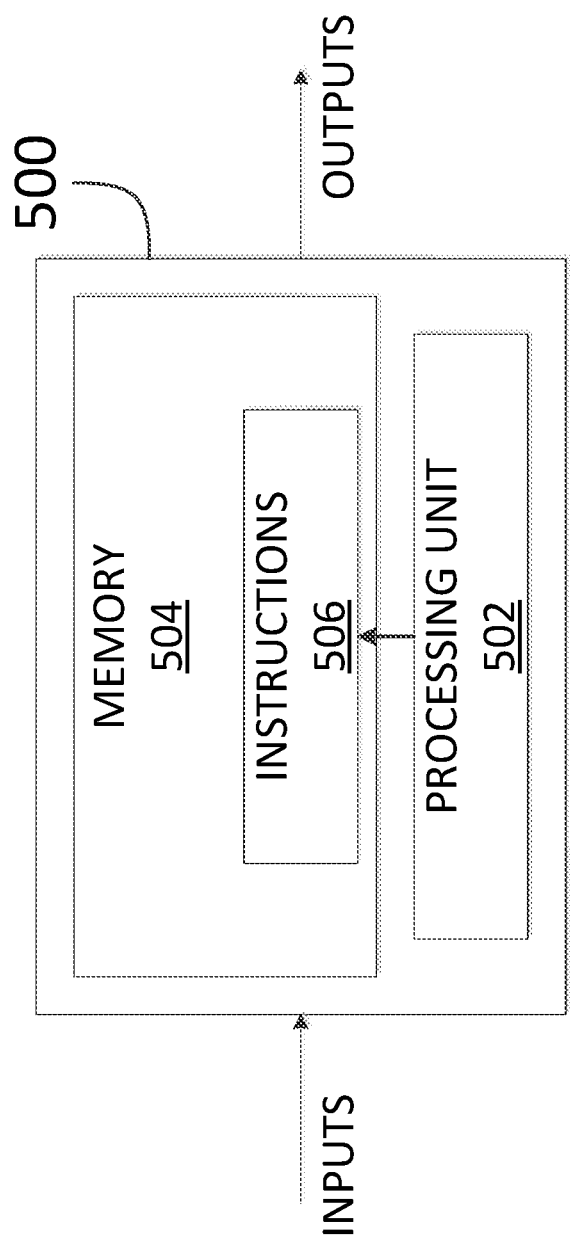
FIG. 4 is a block diagram of an example computing device for implementing the method of FIGS. 2A to 2F in accordance with an embodiment.

With reference to FIG. 4, the method 200 may be implemented by a computing device 500, comprising a processing unit 502 and a memory 504 which has stored therein computer-executable instructions 506. The processing unit 502 may comprise any suitable devices configured to implement the system such that instructions 506, when executed by the computing device 500 or other programmable apparatus, may cause the functions/acts/steps of the method 200 as described herein to be executed. The processing unit 502 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 504 may comprise any suitable known or other machine-readable storage medium. The memory 504 may comprise non-transitory computer readable storage medium, for example, but not limited to, an electronic, magnetic, optical, electromagnetic, infrared, or semiconductor system, apparatus, or device, or any suitable combination of the foregoing. The memory 504 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 504 may comprise any storage means (e.g., devices) suitable for retrievably storing machine-readable instructions 506 executable by processing unit 502.

The methods and systems for predicting an engine condition described herein may be implemented in a high level procedural or object oriented programming or scripting language, or a combination thereof, to communicate with or assist in the operation of a computer system, for example the computing device 500. Alternatively, the methods and systems for predicting an engine condition may be implemented in assembly or machine language. The language may be a compiled or interpreted language. Program code for implementing the methods and systems predicting an engine condition may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems for predicting an engine condition may also be considered to be implemented by way of a non-transitory computer-readable storage medium having a computer program stored thereon. The computer program may comprise computer-readable instructions which cause a computer, or in some embodiments the processing unit 502 of the computing device 500, to operate in a specific and predefined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

Figure 5:
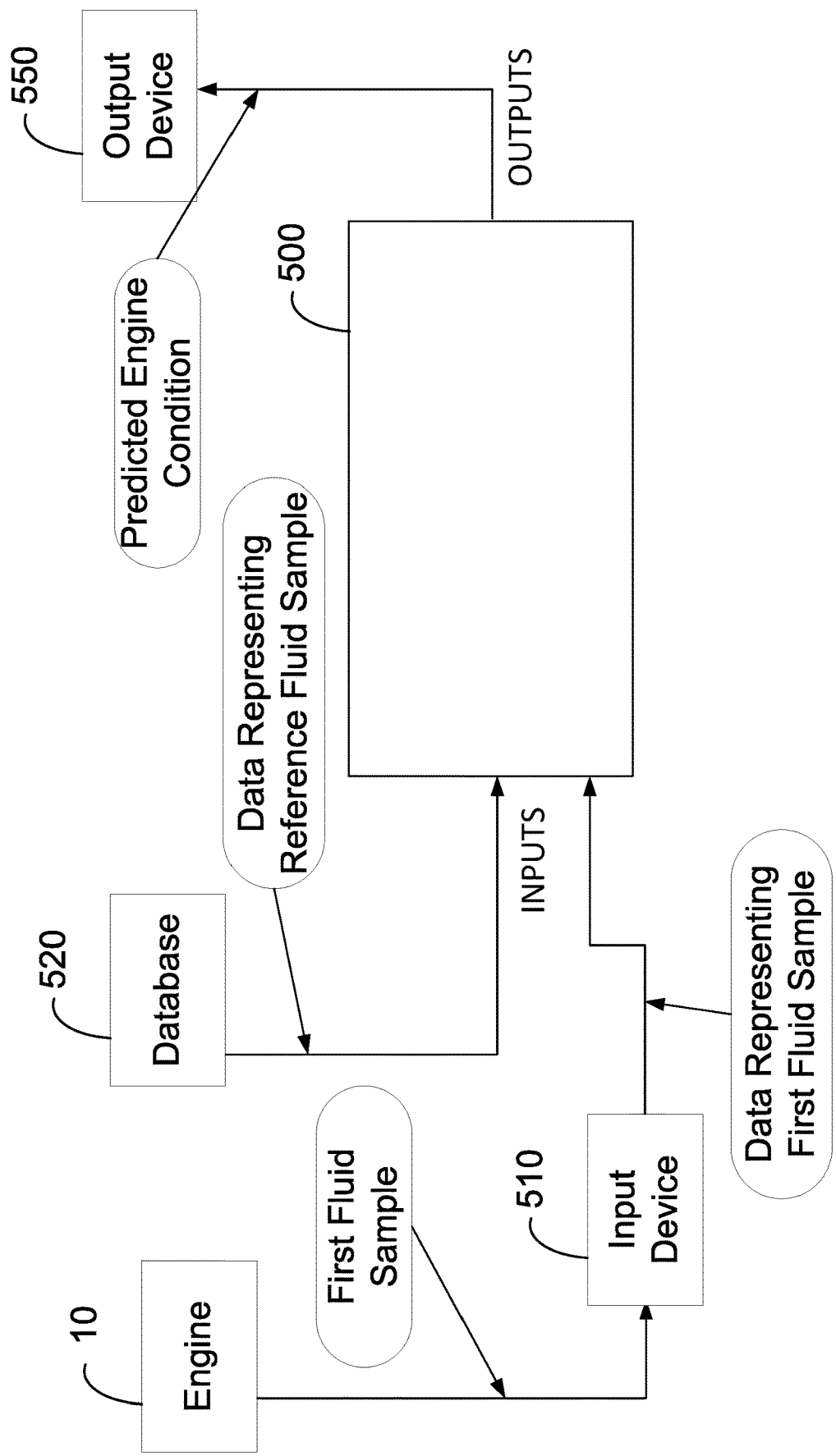
FIG. 5 is a block diagram of on an example computing system configured for predicting the engine condition in accordance with an embodiment.

FIG. 5 illustrates a specific and non-limiting example of implementation of a system for predicting an engine condition. In this example, a first fluid sample is taken from the engine 10 and the input device 510 processes the first fluid sample to obtain data representing the first fluid sample. The input device 510 may comprise one or more of the physical devices/systems described elsewhere in this document, such as SEM, XRF, etc. The data representing the first fluid sample is inputted into the computing device 500 from the input device 510. In this example, the computing device 500 obtains data representing a reference fluid sample from a database 520. The computing device 500 may perform the method 200 to predict an engine condition. The computing device outputs the predicted engine condition to an output device 550 (e.g., a display device, a printer, a networked device or any other suitable output device).

While examples are described herein with reference to an aircraft engine, the method and system for predicting an engine condition described herein may be used with reference to other types of engines.

In some embodiments, the zoning and profiling approach may be used for quality assurance or for calibration of equipment.

It should be appreciated that the zoning and profiling approach may allow for a better comparison of one single engine test with other engine tests with known performance issues. The comparison may take into consideration the fact that each failure mode may have its own characteristic profile.

It should further be appreciated that a particular engine type may be known to have certain failure patterns. Accordingly, the zoning and profiling approach may be used to determine that an engine has a likelihood of a failure pattern. It should further be appreciated that two or more engine types may share the same or similar mechanism of failure. Accordingly, the zoning and profiling approach may be used to determine mechanism of failure.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the methods and systems for predicting an engine condition may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be obvious to those skilled in the art that changes and modifications may be made without departing from this invention in its broader aspects. The scope of the following claims should not be limited by the embodiments set forth in the examples, but should be given the broadest reasonable interpretation consistent with the description as a whole.

What is claimed is:

1. A method for predicting a condition of an engine, the method comprising:

receiving a fluid sample from the engine, the fluid sample having particles suspended therein;

extracting a plurality of particles from the fluid sample;

obtaining a sample profile of the plurality of particles extracted from the fluid sample and obtaining a reference profile of particles of a reference fluid sample from a reference engine, the reference profile and the sample profile having particles identified based on size, aspect ratio and chemical composition;

determining, using size and aspect ratio as axes of a two-dimensional coordinate system, a plurality of average distances between the particles in each of the sample profile and the reference profile and a respective center of each of the sample profile and the reference profile;

determining a correlation index between the sample profile and the reference profile based on the plurality of average distances;

generating, from the correlation index, a prediction that the engine has a known condition associated with the reference engine; and generating, based on the prediction, an output indicating the condition of the engine.

2. The method of claim 1, wherein obtaining the sample profile comprises:

obtaining data representing a first plurality of particles extracted from the fluid sample;

identifying a first set of particles from the first plurality of particles, each particle in the first set of particles having a chemical composition satisfying a chemical composition criteria; and identifying the sample profile from the first set of particles, each particle in the sample profile having a size and an aspect ratio satisfying a profile criteria.

3. The method of claim 2, wherein obtaining the reference profile comprises:

obtaining data representing a second plurality of particles extracted from the reference fluid sample;

identifying a second set of particles from the second plurality of particles, each particle in the second set of particles having a chemical composition satisfying the chemical composition criteria; and identifying the reference profile from the second set of particles, each particle in the reference profile having a size and an aspect ratio satisfying the profile criteria.

4. The method of claim 1, wherein determining the plurality of average distances comprises:

determining a first average distance between particles in the sample profile and the center of the sample profile;

determining a second average distance between particles in the reference profile and the center of the reference profile;

determining a third average distance between particles in the sample profile and the center of the reference profile; and determining a fourth average distance between particles in the reference profile and the center of the sample profile.

5. The method of claim 4, wherein determining the correlation index comprises:

determining a first ratio of the third average distance and the first average distance;

determining a second ratio of the fourth average distance and the second average distance; and computing the correlation index as a product of the first ratio and the second ratio.

6. The method of claim 2, wherein the chemical composition of a given particle satisfies the chemical composition criteria when a concentration range of at least one element of the given particle is within a predetermined range.

7. The method of claim 2, wherein the size of a given particle satisfies the profile criteria when the size of the given particle is within a lower size limit and an upper size limit and the aspect ratio of the given particle satisfies the profile criteria when the aspect ratio of the given particle is within a lower aspect ratio limit and an upper aspect ratio limit, wherein the lower size limit, the upper size limit, the lower aspect ratio limit, and the upper aspect ratio limit are percentiles of the size and aspect ratio of the particles of the first set of particles.

8. The method of claim 1, wherein obtaining the sample profile comprises obtaining a plurality of sample profiles, each one of the plurality of sample profiles determined from a respective one of a plurality of fluid samples from the engine, and wherein determining the correlation index comprises:

determining a profile correlation index for each one of the plurality of sample profiles;

determining a weighting factor for each profile correlation index, the weighting factor based on a population of particles of a respective one of the plurality of sample profiles;

weighting each profile correlation index by the corresponding weighting factor to determine a plurality of weighted correlation indices; and determining the correlation index as a function of the plurality of weighted correlation indices.

9. The method of claim 1, wherein obtaining the sample profile comprises obtaining a plurality of sample profiles of particles of the fluid sample, each one of the plurality of sample profiles having particles with a chemical composition satisfying a respective one of a plurality of chemical composition criteria, wherein obtaining the reference profile comprises obtaining a plurality of reference profiles of particles, each one of the plurality of reference profiles having particles with a chemical composition satisfying a respective one of the plurality of chemical composition criteria, and wherein determining the correlation index comprises:

determining a zone correlation index for each one of the plurality of sample profiles;

determining a weighting factor for each zone correlation index, the weighting factor based on a population of particles of a respective one of the plurality of sample profiles;

weighting each zone correlation index by the corresponding weighting factor to determine a plurality of weighted correlation indices; and determining the correlation index as a function of the plurality of weighted correlation indices.

10. The method of claim 1, wherein the reference engine is the engine.

11. A system for predicting a condition of an engine, the system comprising:

at least one processing unit; and a non-transitory computer-readable memory having stored thereon program instructions executable by the at least one processing unit for:

obtaining a sample profile of a plurality of particles extracted from a fluid sample and obtaining a reference profile of particles of a reference fluid sample from a reference engine, the reference profile and the sample profile having particles identified based on size, aspect ratio and chemical composition;

determining, using size and aspect ratio as axes of a two-dimensional coordinate system, a plurality of average distances between the particles in each of the sample profile and the reference profile and a respective center of each of the sample profile and the reference profile;

determining a correlation index between the sample profile and the reference profile based on the plurality of average distances;

generating, from the correlation index, a prediction that the engine has a known condition associated with the reference engine; and generating, based on the prediction, an output indicating the condition of the engine.

12. The system of claim 11, wherein obtaining the sample profile comprises:

obtaining data representing a first plurality of particles extracted from the fluid sample;

identifying a first set of particles from the first plurality of particles, each particle in the first set of particles having a chemical composition satisfying a chemical composition criteria; and identifying the sample profile from the first set of particles, each particle in the sample profile having a size and an aspect ratio satisfying a profile criteria.

13. The system of claim 12, wherein obtaining the reference comprises:

obtaining data representing a second plurality of particles extracted from the reference fluid sample;

identifying a second set of particles from the second plurality of particles, each particle in the second set of particles having a chemical composition satisfying the chemical composition criteria; and identifying the reference profile from the second set of particles, each particle in the reference profile having a size and an aspect ratio satisfying the profile criteria.

14. The system of claim 11, wherein determining the plurality of average distances comprises:

determining a first average distance between particles in the sample profile and the center of the sample profile;

determining a second average distance between particles in the reference profile and the center of the reference profile;

determining a third average distance between particles in the sample profile and the center of the reference profile; and determining a fourth average distance between particles in the reference profile and the center of the sample profile.

15. The system of claim 14, wherein determining the correlation index comprises:

determining a first ratio of the third average distance and the first average distance;

determining a second ratio of the fourth average distance and the second average distance; and computing the correlation index as a product of the first ratio and the second ratio.

16. The system of claim 12, wherein the chemical composition of a given particle satisfies the chemical composition criteria when a concentration range of at least one element of the given particle is within a predetermined range.

17. The system of claim 12, wherein the size of a given particle satisfies the profile criteria when the size of the given particle is within a lower size limit and an upper size limit and the aspect ratio of the given particle satisfies the profile criteria when the aspect ratio of the given particle is within a lower aspect ratio limit and an upper aspect ratio limit, wherein the lower size limit, the upper size limit, the lower aspect ratio limit, and the upper aspect ratio limit are percentiles of the size and aspect ratio of the particles of the first set of particles.

18. The system of claim 11, wherein the reference engine is the engine.

* * * * *